United States Patent [19]

Berger et al.

[11] Patent Number: 4,996,202

[45] Date of Patent: Feb. 26, 1991

[54] 1,2,4,5 TETRAHYDRO BENZAZEPINE-3 COMPOUNDS AND ANTIPSYCHOTIC USE THEREOF

[75] Inventors: Joel G. Berger, Cedar Grove; Wei K. Chang, Livingston; Elijah H. Gold, West Orange, all of N.J.; Arthur J. Elliott, Sloatsburg, N.Y.

[73] Assignee: Schering Corporation, Kenilworth, N.J.

[21] Appl. No.: 788,274

[22] Filed: Oct. 17, 1985

Related U.S. Application Data

[63] Continuation-in-part of Ser. No. 522,948, Aug. 12, 1983, abandoned.

[51] Int. Cl.$^5$ .................. C07D 223/16; C07D 413/04; C07D 403/04; A61K 31/55
[52] U.S. Cl. .................................... 514/213; 540/593; 540/594
[58] Field of Search ................. 260/239 BB; 514/213; 540/593, 594

[56] References Cited

U.S. PATENT DOCUMENTS

| 3,395,150 | 7/1968 | Krapcho | 540/593 |
| 4,210,749 | 7/1980 | Shetty | 540/593 |
| 4,284,555 | 8/1981 | Gold et al. | 260/239 BB |
| 4,284,556 | 8/1981 | Holden et al. | 260/239 BB |

OTHER PUBLICATIONS

Benson et al., Tranquilizing and Anti-Depressive Drugs; Thomas, Springfield, Ill., 1962, pp. 65-67.

*Primary Examiner*—David B. Springer
*Attorney, Agent, or Firm*—Warrick E. Lee, Jr.; James R. Nelson

[57] ABSTRACT

Substituted 8-amino-1-phenyl-2,3,4,5-tetrahydro-1H-3-benzazepines useful in treating mental disorders and which have activities of prolonged duration are disclosed. Methods for preparing these compounds and methods for their use are also described.

35 Claims, No Drawings

1,2,4,5 TETRAHYDRO BENZAZEPINE-3 COMPOUNDS AND ANTIPSYCHOTIC USE THEREOF

This application is a continuation-in-part of U.S. application Ser. No. 522,948, filed Aug. 12, 1983, abandoned.

BACKGROUND OF THE INVENTION

British patent specification No. 1,268,243 generically discloses a class of benzazepines which may contain an 8-amino and a 1-phenyl substituent. The specification does not specifically describe these compounds, nor does it disclose how the 8-amino-1-phenyl substituted benzazepines may be prepared. The disclosed compounds are described as having analgesic antihistaminic, anticholinergic and narcotic antagonist properties.

The present invention provides certain substituted 8-amino-1-phenyl-2,3,4,5-tetrahydro-1H-3-benzazepines which are useful in the treatment of mental disorders such as psychoses and depression.

SUMMARY OF THE INVENTION

The invention sought to be patented in its chemical compound aspect is a compound of structural formula I, having the depicted absolute stereochemical configuration at carbon 1, which is usually designated as the R configuration

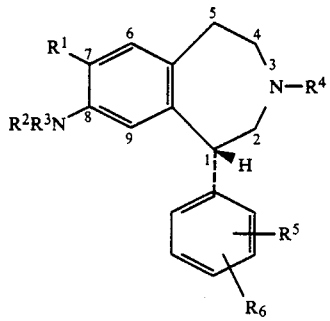

wherein $R^1$ may be hydrogen, halogen, alkyl, alkoxy, or trifluoromethyl;

$R^2$ may be hydrogen, alkyl, arylalkyl or $COXR^a$ (wherein $R^a$ is hydrogen or alkyl and X is a bond or NH);

$R^3$ may be hydrogen or alkyl;

$R^2$ and $R^3$ may be taken together with the nitrogen atom to which they are attached to form

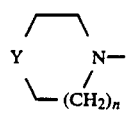

wherein Y is O, $CH_2$ or $NR^a$ (wherein $R^a$ is as defined above) and n is 0, 1 or 2, provided that n is not 0 when Y is O or $NR^a$;

$R^4$ may be alkyl, $-CH_2CH=CH_2$ or

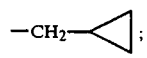

$R^5$ and $R^6$ may be the same or different and are independently selected from hydrogen, alkyl, trifluoromethyl, halogen, $OR^a$ (wherein $R^a$ is defined above) or together may form $-OCH_2O-$; and the pharmaceutically acceptable salts thereof.

The compounds of the invention provide activities of relatively long duration useful in the treatment of disorders such as psychoses and depression.

Preferred definitions for the above described substituents are as follows:

$R^1$ is halogen, methyl or trifluoromethyl;

$R^2$ is hydrogen, methyl, formyl or acetyl;

$R^3$ is hydrogen;

$R^4$ is methyl or $-CH_2CH=CH_2$;

$R^5$ is hydrogen, methyl, halogen or $OR^a$ (wherein $R^a$ is defined above); and $R^6$ is hydrogen.

A preferred species of the invention is (R)-8-amino-7-chloro-3-methyl-1-phenyl-2,3,4,5-tetrahydro-1H-3-benzazepine.

The invention sought to be patented in its pharmaceutical composition aspect is a composition useful for treating metal disorders such as psychoses and/or depression in a mammal which comprises a compound having structural formula I or a pharmaceutically acceptable salt thereof in combination with a pharmaceutically acceptable carrier.

The invention sought to be patented in a first pharmaceutical method aspect is a method for treating psychoses in a mammal which comprises administering an effective amount of the above-defined pharmaceutical composition to said mammal.

The invention sought to be patented in a second pharmaceutical method aspect is a method for treating depression in a mammal which comprises administering an effective amount of the above-defined pharmaceutical composition to said mammal.

DESCRIPTION OF THE INVENTION

The compounds of the invention having structural formula I wherein $R^2=R^3=H$ may be prepared from the correspondingly substituted 8-hydroxy compounds by methods known in the art. These compounds may next be readily converted to other desired compounds of the invention wherein $R^2$ and $R^3$ may be other than hydrogen.

In the following discussion, the 8-substituted benzazepine moiety will be represented by the symbolic formula I' for reasons of convenience:

(substituent) — ⓑ      I'

The symbol

— ⓑ represents the partial structure

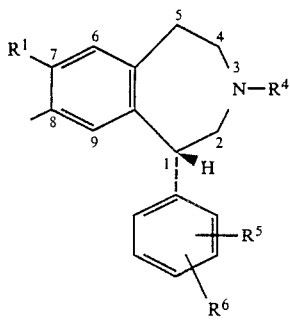

and has the indicated substituent bonded at the 8-position.

A convenient starting material useful for obtaining the desired compounds,

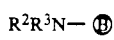

is the correspondingly substituted 8-hydroxybenzazepine having the symbolic formula

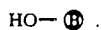

Thus, an 8-hydroxy-substituted benzazepine may be treated with acetone and chloroform in the presence of base {see for example, Synthesis, 31(1977)} to produce a carboxylate salt having the formula

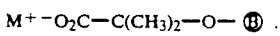

$M^+$ represents a metal cation such as a sodium or a potassium cation which is derived from the particular base that was utilized in the reaction. Those skilled in the art will recognize that the use of a base comprising a multivalent metal such as calcium will produce a corresponding salt, e.g.,

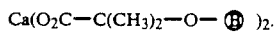

The so produced carboxylate salt may next be converted to the corresponding acid halide such as the acid chloride by treatment with, for example, thionyl chloride. The so produced acid halide may next be converted to the corresponding acid amide by treatment with concentrated ammonium hydroxide in a suitable solvent such as tetrahydrofuran. The so produced acid amide having the formula

may next be converted to the acyl anilide having the formula

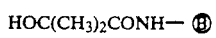

by treatment with a strong base in a suitable solvent, e.g., sodium hydride in N,N-dimethylformamide {see for example, Organic Reactions, 18, 99 (1970)}. The so obtained amide may be converted to the corresponding amine,

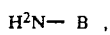

i.e., compound I wherein $R^2=R^3=H$, by hydrolysis, example hydrolysis with 50% sulfuric acid solution.

If desired, the so obtained amine may be reacted with an acylating agent such as $ClSO_2R^b$, $R^bCOCl$, $(R^cCO)_2O$, $R^bNCO$, $R^bNHCOCl$, urea/HCl and other acylating agents known in the art to produce the corresponding sulfonamide

carboxamide

or urea

in {wherein $R^b$ is alkyl, aryl or arylalkyl and wherein $R^c$ is hydrogen, alkyl, aryl or arylalkyl}. With exceptions, such as when acylating with urea/HCl, this reaction is often preferably carried out in the presence of an organic tertiary amine base such as triethylamine, N-methyl morpholine, pyridine or a weak inorganic base such as $NaHCO_3$ or $K_2CO_3$. Many of the so produced carboxamides or ureas are, of course, products of the invention having structural formula I, wherein $R^2$ is $R^aCO$ and $R^aNHCO$ and wherein $R^a$ is as defined herein ($R^c$ being $R^a$ in this instance).

The carboxamido derivatives having the respective formulae

wherein $R^c$ is defined herein may be reduced with, for example, lithium aluminum hydride or diborane to produce a substituted amine

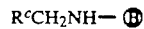

i.e., wherein $R^2$ is $R^cCH_2$ which in this case represents alkyl or arylalkyl.

If desired, the so obtained amine,

wherein $R^2$ is alkyl or arylalkyl, may be acylated with an appropriate acylating agent as described above for the acylation of

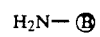

to produce the corresponding disubstituted carboxamido derivatives having the formula

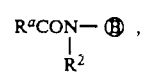

wherein $R^a$ is as defined herein (with $R^a$ being $R^b$ or $R^c$ depending on the acylating agent).

Alternatively, the amides having the respective formulae

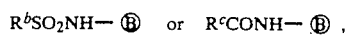

may be alkylated for example with an alkyl halide or arylalkyl halide, such as alkyl bromide or arylalkyl bromide. This alkylation may be carried out by known procedures, for example, by the use of sodium hydride to produce a disubstituted amide (i.e., a sulfonamide or carboxamide) having the respective structure

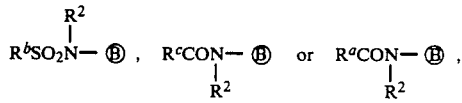

wherein $R^2$ is alkyl or arylalkyl and $R^3$ is alkyl.

Said disubstituted amides may be reduced, for example, with lithium aluminum hydride to produce (1) the corresponding tertiary amine (from the carboxamides), having the formula

wherein $R^2$ is alkyl or arylalkyl and $R^3$ is alkyl, or (2) the corresponding secondary amine

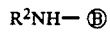

(from the sulfonamide), wherein $R^2$ is alkyl or arylalkyl. Alternatively, the disubstituted carboxamides may be treated with a base to remove the acyl group, $R^aCO$ or $R^cCO$, and thereby produce the corresponding secondary amine,

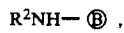

wherein $R^2$ is alkyl or arylalkyl.

In the above described conversion sequences, the proper selection of the acylating agent (e.g., $R^bCOCl$) and alkylating agent (e.g. alkyl bromide) will permit the preparation of compounds of formula I, i.e.

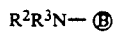

Other methods for obtaining compounds of formula I,

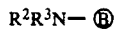

from compounds

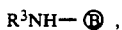

wherein $R^2$ may be alkyl or arylalkyl and $R^3$ herein defined, are well known in the art. Thus, for example, compounds

can be reductively alkylated with a suitable aldehyde or ketone, $R^aR^cCOR$, in the presence of a suitable reducing agent such as $NaCNBH_3$ in an appropriate solvent such as methanol to produce an amine having the structure

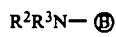

wherein $R^2$ is $R^aR^cCH_2$ and represents alkyl or arylalkyl and $R^3$ is as herein defined.

When $R^3$ is hydrogen, this procedure may be repeated to produce compounds

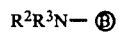

wherein $R^3$ is alkyl and $R^2$ is alkyl or arylalkyl.

Compounds having structural formula I, wherein $R^2$ and $R^3$ are taken together with the nitrogen atom to which they are attached to form a ring, may be prepared from the corresponding compounds having structural formula I wherein $R^2$ and $R^3$ are both hydrogen. For example, the primary amino compound may be reacted with an acylating agent such as an acid chloride having the structural formula $L(CH_2)_nCH_2-YCH_2COCl$ wherein L is a leaving group such as halogen and Y and n are defined herein to produce the amides having the structural formula

This carboxamide may be reduced to the corresponding amine, for example with diborane, and cyclized by heating in the presence of an acid acceptor such as pyridine to produce the cyclic amine having the following structural formula

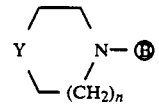

The carboxamides may also be cyclized, for example, by use of sodium hydride, to produce the corresponding cyclic amides having the structural formula

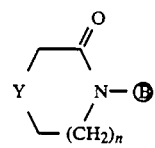

This cyclic carboxamide may also be reduced, for example by use of lithium aluminum hydride, to produce the same cyclic amine described above.

In order to obtain products of this invention having structural formula I, wherein $R^5$ and/or $R^6$ is hydroxy, it will be clear to those skilled in the art that the oxygen substituent or substituents should be suitably protected during many of the above-described chemical transformations. A convenient protecting group is benzyl for example.

The 8-hydroxy-substituted benzazepine compounds

may be prepared for example by methods described in U.S. Pat. No. 3,393,192 or by art recognized variations thereof.

When utilized herein and in the appended claims the below listed terms, unless specified otherwise, are defined as follows:

halogen—fluorine, chlorine, bromine and iodine;
alkyl and alkoxy—comprised of straight and branched carbon chains containing from 1 to 6 carbon atoms;

aryl-unsubstituted phenyl and phenyl monosubstituted by alkyl, hydroxy, alkoxy, halogen or trifluoromethyl.

The compounds of the invention display pharmacological activity in test procedures designed to show antipsychotic and antidepressant activity.

ANTIPSYCHOTIC POTENTIAL

Blockade Of Amphetamine-Induced Lethality In Aggretated Mice

Amphetamines are known to be more lethal in grouped than singly-housed mice {Psychopharmacolgia, 1, 210 (1960)}. Standard antipsychotic drugs are potent antagonists of this aggregate toxicity {Arch. Int. Pharmacodyn, 113, 290 (1958)} and the ability of drugs to antagonize amphetamine-induced lethality is used to predict antipsychotic potency {Arzneim.-Forsch.(Drug Research), 25, 1436 (1975)}.

METHODS AND MATERIAL

Methamphetamine was used to produce lethality in groups of ten mice housed in 11×26×13 cm plastic chambers. Test drugs were administered 30 minutes prior to intraperitoneal injection of methamphetamine at 15 mg/kg, a dose that typically killed at least 90% of the mice within 4 hours. The number of deaths in each group was recorded 4 hours after methamphetamine administration. The dose of each test compound that provided 50% protection ($ED_{50}$) and the 95% confidence limits (95% CL) were determined using probit analysis.

RESULTS

A representative compound of the invention (R)-8-amino-7-chloro-3-methyl-1-phenyl-2,3,4,5-tetrahydro-1H-3-benzazepine caused dose-related blockade of methamphetamine induced lethality of grouped mice and had an $ED_{50}=13.5$ mg/kg when given by the oral route.

Representative compounds of the invention also displayed activity when tested as follows:

CONDITIONED AVOIDANCE SUPPRESSION IN RATS

Clinically active antipsychotic drugs are known to depress discrete trial avoidance behavior at doses that do not retard escape responding {Ann. N.Y. Acad. Sci., 66, 740 (1957)}. A series of experiments was carried out to assess the ability of the compounds of the invention to suppress the conditioned avoidance response (CAR) in rats.

METHODS AND MATERIALS

Rats were required to jump onto a platform located 6¾ inches above the grid floor of an experimental chamber in response to a 5-second tone to avoid a ten-second foot shock (0.6 ma). Each experimental session consisted of 20 such trials presented at 30-second intervals. A correct CAR occurred whenever the rat jumped onto the platform during the tone (prior to foot shock). An escape response occurred when the rat jumped onto the platform during shock. A response failure is defined as the lack of an escape response during the 10-second shock period.

Groups of 6–8 rats were trained on two consecutive days (total of 40 trials). Rats that reached criterion on day 2 (correct CARs on 16 or more of the 20 trials) were treated with either a test drug or vehicle on day 3. Suppression of CAR was analyzed statistically using Student's t-test comparing the performance of drug-treated to vehicle-treated rats. The minimal effective dose (MED) for each drug is defined as the lowest dose tested that significantly ($P<0.05$) reduced avoidance responding.

RESULTS

A representative compound of the invention, (R)-8-amino-7-chloro-3-methyl-1-phenyl-2,3,4,5-tetrahydro-1H-3-benzazepine when tested by the above procedure manifested a dose-related specific blockade of conditioned avoidance responding with an MED of 2.5 mg/kg (oral) at 1 and 4 hours after dosing.

ANTIDEPRESSANT POTENTIAL

Effects On Tetrabenazine (TBZ)-Induced Ptosis In Mice6

Clinically active antidepressant drugs are known to block TBZ-induced ptosis in mice (Psychosomatic Medicine, Nodine and Moyer, Eds., Lea and Febiger, Philadelphia, 1962, pp 683–90). Activity in this test is used to predict anti-depressant activity in man.

METHODS AND MATERIALS

Groups of 5 mice were administered test drugs followed 30 minutes later by ip injection of tetrabenazine, 30 mg/kg. Thirty minutes later, the degree of ptosis was evaluated. Percent blockade of each treated group was used to determine $ED_{50}$'s, defined as that dose which prevents ptosis in 50% of mice. $ED_{50}$'s and 95% confidence limits were calculated by probit analysis.

RESULTS (R)-8-amino-7-chloro-3-methyl-1-phenyl-2,3,4,5-tetrahydro-1H-3-benzazepine, a representative compound of the invention, caused antagonism of TBZ-induced ptosis in mice at an $ED_{50}$ of 3 mg/kg when administered orally.

EFFECTS ON MURICIDE ACTIVITY IN RATS

Blockade of muricide (mouse-killing) activity in rats has been used as a measure of evaluating the antidepressant activity of drugs (Int. J. Neuropharmacol., 5, 405–11 (1966)).

METHODS AND MATERIALS

Groups of 5 rats were administered test drug intraperitonially and tested 30 and 60 minutes later for presence of muricide activity. Percent blockade of each treated group using data obtained at both these time points was calculated and dose-response data were used to determine each $ED_{50}$. $ED_{50}$ is defined as that dose which blocks muricide behavior in 50% of treated rats and was calculated using probit analysis.

RESULTS

A representative compound of this invention, (R)-8-amino-7-chloro-3-methyl-1-phenyl-2,3,4,5-tetrahydro-1H-3-benzazepine blocked muricide behavior at an $ED_{50}$ of 2.7 mg/kg.

The compounds of the invention possess an asymetric carbon atom, i.e. carbon number 1 in structural formula I. The R form in the above formula I has the hydrogen atom at this position depicted as being bonded in the β or "up" configuration. A heavy bond ( ) is utilized to indicate that the hydrogen atom is above the plane of the page.

Pharmaceutical activity, as described above, of the compounds having structural formula I has only been observed for compounds having the R stereochemical configuration at this asymetric center. Thus, racemates of these and other mixtures of the R form will also provide such pharmaceutical activity and therefore such racemates and mixtures are also intended to be included with the broad scope of the present invention. Compositions and methods employing the substantially pure R form of the compound are, however, preferred.

The compounds of the invention of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

Certain compounds of the invention from pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and the like. The salts are prepared by contacting the free base form with a sufficient amount of the desired acid to produce a salt in the conventional manner. The free base forms may be regenerated by treating the salt form with a base. For example, dilute aqueous base solutions may be utilized Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

For preparing pharmaceutical compositions from the compounds described by this invention, inert, pharmaceutically acceptable carriers can be either solid or liquid. Solid form preparations include powders, tablets, dispersible granuals, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form prepartion may be water, isotonic water, ethanol, glycerine, propylene glycol and the like as well as mixtures thereof. Naturally, the solvent utilized will be chosen with regard to the route of administration, or example, liquid preparations containing large amounts of ethanol are not suitable for parenteral use.

The invention also contemplates mechanical delivery systems, e.g. transdermal delivery.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg. according to the particular application and the potency of the active ingredient. The composition can, if desired, also contain other therapeutic agents.

The dosages may be varied depending upon the requirement of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

EXAMPLE I (R)-8-Amino-7-chloro-3-methyl-1-phenyl-2,3,4,5-tetrahydro-1H-3-benzazepine

A.

(R)-1,1-Dimethyl-(7-chloro-3-methyl-1-phenyl-2,3,4,5-tetrahydro-1H-3-benzazepine-8-yl-oxy)acetamide Sodium hydroxide (20.0g 0.5 mol) was added to a stirred solution of (R)-7-chloro-8-hydroxy-3-methyl-1-phenyl-2,3,4,5-tetradhydro-1H-3-benzazepine (21.6g 0.075 mol) in acetone (900 ml) and the mixture was heated to reflux to effect solution. Chloroform (13.4g, 0.112 mol) was added dropwise during one hour and then the mixture was heated under reflux for 5 hours and allowed to cool.

The solid was filtered off, washed with ether and dried. Yield 47.6 g. This material was added with and stirring continued for ½ hour. The excess thionyl chloride was evaporated below 50° and the residue was dissolved in dry THF and added to stirred conc. NH3. After the addition (1 hr) the mixture was allowed to stand overnight.

The solid was filtered off, washed with water and dried. Yield 17.2 g light brown powder. This was dissolved in CHCl3 and passed through a filter of silica gel. The filtrate was evaporated and the residue crystallized from chlorobutane to give 13.2 g of pale lemon colored needles m.p. 151°-153° C. $[\alpha]^{26}_D 52.9°$ (DMF,c=1)

B.

(R)-7-Chloro-8-[N-(2-hydroxy-2-methylpropionyl)]-amino-3-methyl-1-phenyl-2,3,4,5-tetrahydro-1H-3-benzazepine The product obtained in Part A (13.2g 0.0356 mol) was dissolved in anhydrous DMF (120 ml) and 50% sodium hydride in mineral oil 1.71 g 0.0356 mol) was added. The mixture was heated and stirred to 110° under nitrogen for 24 hours.

The mixture was cooled and poured onto icewater (1200 ml). The precipitated white solid was filtered off and dried in vacuo.

Crystallization from chlorobutane gave 10.3 g of colorless solid, m.p. 174°-176° C. $[\alpha]^{26}_D 66.6°$(DMF,c=1)

C.

(R)-8-Amino-7-chloro-3-methyl-1-phenyl-2,3,4,5-tetrahydro-1H-3-benzazepine

The product obtained in Part B (110.0g) was added to 400 ml. of 50% sulfuric acid, the mixture stirred at 100° for 2 hrs. then allowed to cool. The solution was then poured into 2l. of 6n NaOH, and extracted with two 1l. portions of ethyl acetate. The combined extracts were washed with water (1l.), dried over anhyd MgSO4 and evaporated in vacuo. The resulting oil was recrystallized from ethanol to give 50.1 g. of product as a monoethanolate, m.p. 68°-70° C., $[\alpha]^{26}_D 50.7°$(DMF,c=1)

EXAMPLE II (R)-8-Amino-7-chloro-3-methyl-1-phenyl-2,3,4,5,-tetrahydro-1H-3-benzazepine, maleate salt 14.1 g. of the free base of example I was dissolved in warm ethyl acetate (300 ml.), and maleic acid (4.92 g.) added. The resulting mixture was brought to reflux, then allowed to cool. The resulting solid was filtered and recrystallized from ethanol to give colorless crystals of the maleate, m.p. 203°-5° C.,$[\alpha]^{26}_D 2.9°$(DMF,c=1)

EXAMPLE III (R)-8-Formamido-7-chloro-3-methyl-1-phenyl-2,3,4,5-tetrahydro-1H-3-benzazepine Formic acid (2.25 g, 95-97%) was added dropwise to acetic anhydride (4.10 g.) at 0° C. with stirring. The resulting solution was heated under nitrogen in a water bath at 50°-60° C. with stirring for 2 hours longer. The solution was cooled down to room temperature and diluted with 5 ml of THF. A solution of (R)-8-amino-7-chloro-3-methyl-1-phenyl-2,3,4,5-tetrahydro-1H-3-benzazepine (5.10 g, 0.018 mol) in 25 ml of THF was added dropwise with stirring to the above solution. The resulting solution was stirred at room temperature for 3.5 hours longer and left standing at room temperature for 24 hours. The THF was evaporated in vacuo and the residue was treated with ether and 1N Na2CO3. The dried ether solution was evaporated in vacuo. The residue crystallized from acetonitrile, m.p. 135°-136° C. $[\alpha]^{26}_D +72.6°$ C. (DMF, c=1).

EXAMPLE IV (R)-8-Methylamino-7-chloro-3-methyl-1-phenyl-2,3,4,5-tetrahydro-1H-3-benzazepine 2 Mol BH3.Me2S in THF (13.25 ml) was added dropwise to the product obtained in Example III (2.55 g, 0.008 mol) dissolved in 30 ml of THF with stirring and cooling in an ice bath. The ice bath was removed and the mixture was heated to reflux for 3.5 hours. The mixture was left to stand at room temperature overnight. Ethanolic HCl was added dropwise to the mixture with cooling (ice bath) and stirring until a pH of 1.5 was reached. The mixture was heated to reflux for one hour and then the solvent was removed. The residue was stirred with ether and 1N NaOH. The dried ether solution was evaporated in vacuo. The residue was crystallized from isopropyl ether, m.p. 98°-100° C. $[\alpha]^{26}_D +67.3$ (DMF, c=1).

EXAMPLE V (R)-8-Amino-3,7-dimethyl-1-phenyl-2,3,4,5-tetrahydro-1H-3-benzazepine

A.

(R)-3,7-dimethyl-8-(1-phenyl-1H-tetrazol-5-yl)oxy-1-phenyl-2,3,4,5-tetrahydro-1H-3-benzazepine (R)-8-Hydroxy-3,7-dimethyl-1-phenyl-2,3,4,5-tetrahydro-1H-3-benzazepine (13.35g, 0.0499 mol) was dissolved in DMF (70 ml) and 50% sodium hydride in mineral oil (2.4 g, 0.0499 mol) was added with stirring under nitrogen. The solution was stirred at room temperature for one hour longer. A solution of 5-chloro-1-phenyl-1H-tetrazole (9.90 g) in DMF (40 ml) was added dropwise to the solution with stirring. The solution was stirred for two hours longer and then at 45° C. for another 0.5 hour. The solution was chilled and poured into 900 ml of ice and H2O. The solution was extracted with 2× 250 ml of ether. The combined ethyl layers were washed with 300 ml of water. The ether solution was dried and reduced to about 125 ml. The solid was filtered off, m.p. 140°-142° C.

B.
(R)-3,7-dimethyl-1-phenyl-2,3,4,5-tetrahydro-1H-3-benzazepine

The product obtained in Part A (13.2 g, 0.0032 mol) was reduced in acetic acid (125 ml) with 20% Pd(OH)$_2$/C (1.50 g) at 55° C. until uptake of hydrogen ceased. The catalyst and solvent were removed. The residue was treated with ether and 1N NaOH. The ether layer was dried over K$_2$CO$_3$. The solvent was filtered and removed to give an oily syrup, $[\alpha]^{26}_D +45.1$ (c=1, EtOH).

C.
(R)-8-Nitro-3,7-dimethyl-1-phenyl-2,3,4,5-tetrahydro-1H-3-benzazepine

Trifluoroacetic acid (45 ml) and then CHCl$_3$ (30 ml) was added to a mixture of the product obtained in Part B (6.7 g, 0.0266 mol) and NH$_4$NO$_2$ (2.80 g) with cooling (ice bath) and stirring. The mixture was stirred in an ice bath for 30 minutes and then at room temperature for 2.5 hours. The volume of solution was reduced to about 25 ml by passing thru a stream of nitrogen. The residue was dissolved in 100 ml each of ether and water. Sodium carbonate was added to the solution in small portions with cooling and stirring until basic. The ether layer was dried and the solvent removed. The residue was purified thru a T.L.C. grade silica gel column. The product (2.9 g) of this example was obtained as an oily syrup, $[\alpha]^{26}_D +41.5$ (c=0.5, EtOH).

D.
(R)-8-Amino-3,7-dimethyl-1-phenyl-2,3,4,5-tetrahydro-1H-3-benzazepine

The product obtained in Part C (2.3 g, 0.00776 mol) was reduced in EtOH (75 ml) with 10% Pd/C (300 mg). The catalyst and solvent were removed. The residue was dissolved in ether (40 ml). Insoluble material was removed by filtration. The filtrate was evaporated in vacuo to dryness, giving the product of this example (1.5 g) $[\alpha]^{26}_D +40.4$ (c=0.5, EtOH).

EXAMPLE VI
(R)-8-Amino-3,7-dimethyl-1-phenyl-2,3,4,5-tetrahydro-1H-3-benzazepine maleate The product of Example V, part D above was treated with maleic acid (650 mg) in isopropanol, affording 1.50 g of the product of this example, m.p. 171°–174° C. $[\alpha]^{26}_D +9.80$ (c=0.25, DMF).

EXAMPLE VII
(R)-8-Acetamido-7-chloro-3-methyl-1-phenyl-2,3,4,5-tetrahydro-1H-3-benzazepine A solution of the compound produced in example IC above (5.3 g.) in 100 ml. of acetonitrile was treated with 5 ml. of acetic anhydride and 20 mg. of 4-dimethylaminopyridine. The mixture was allowed to stir at room temperature for 5½ hrs., after which it was evaporated to dryness and 25 ml. of methanol and another 25 mg. of dimethylaminopyridine added. The mixture was treated at reflux for 20 min., cooled, and evaporated to dryness. The residue was stirred with 90 ml. of a 5% Na$_2$CO$_3$ solution, and the solids filtered. Recrystallization of this material from acetonitrile gave 4.05 g. product which was dried in vacuo at 50° to give the desired product, m.p. 105°–110° C., $[\alpha]^{26}_D 39°$(c=1, DMF).

EXAMPLE VIII
(R)-8-Dimethylamino-7-chloro-3-methyl-1-phenyl-2,3,4,5-tetrahydro-1H-3-benzazepine fumarate A suspension of 3.3 g of 8-amino-7-chloro-3-methyl-1-phenyl-2,3,4,5-tetrahydro-1H-3-benzazepine and 160 mg of NaBH$_4$ in 10 ml of tetrahydrofuran was added in small portions to a stirred solution of 3 ml of formaldehyde solution and 10 ml of 3M H$_2$SO$_4$ in 20 ml of tetrahydrofuran. After 10 minutes the mixture was diluted with 25 ml of water and basified with solid KOH. Tetrahydrofuran was removed in vacuo, and the residue was treated with 75 ml of ether with stirring. The ether layer was separated, dried over anhydrous potassium carbonate and evaporated in vacuo. The resulting oily residue was chromatographed on 200 g silica gel using CHCl$_3$/ethyl acetate/NH$_4$OH (50:50:1) as the eluant. This gave the pure oily product of this example as a free base, which was treated with fumaric acid in ethyl acetate solution. The gummy salt so obtained was recrystallized from acetonitrile to give the product of this example, m.p. 155°–157° C.

EXAMPLE IX
(R)-8-Ethylamino-7-chloro-3-methyl-1-phenyl-2,3,4,5-tetrahydro-1H-3-benzazepine

A.
8-Acetamido-7-chloro-3-methyl-1-phenyl-2,3,4,5-tetrahydro-1H-3-benzazepine 3.4 g of 8-amino-7-chloro-3-methyl-1-phenyl-2,3,4,5-tetrahydro-1H-3-benzazepine in 50 ml of methylene chloride was treated with 4 ml of acetic anhydride followed by addition of 10 mg. of 4-dimethylaminopyridine. The resulting mixture was stirred at room temperature for 2 hours, and the solvent was removed in vacuo. The residue was stirred with a mixture of ether and sodium bicarbonate solution for 1 hour. The ether layer was separated, dried over sodium sulfate and evaporated in vacuo. The resulting crude product of this example (3.1 g) was used in the following step B.

B. (R)-8-Ethylamino-7-chloro-3-methyl-1-phenyl-2,3,4,5-tetrahydro-1H-3-benzazepine A solution of the product of Example IX A above in 20 ml of dry ether was added dropwise to a stirred suspension of 380 mg of lithium aluminum hydride in 50 ml of ether. The mixture was then stirred at reflux for 4½ hours and thereafter allowed to stand at room temperature overnight. An additional 100 mg of lithium aluminum hydride was then added, and the mixture heated at reflux with stirring for an additional 2 hours. It was then cooled in an ice bath and treated with dropwise addition of water. Precipitated material was filtered off and washed with ether, and the combined filtrates were dried over MgSO$_4$ and evaporated in vacuo. The residue was chromatographed on 100 g of silica gel, eluting with CHCl$_3$/CH$_3$OH/NH$_4$OH (50:3:1) to yield the product of this example, m.p. 120°–121° C. $[\alpha]_D +67.3°$(c=1, DMF).

Although the present invention has been described in conjunction with the above embodiments, it will be apparent to those skilled in the art that many alternatives, modifications and variations thereof can be employed in light of the foregoing description. All such alternatives, modifications and variations are intended

We claim:
1. A compound having the structural formula:

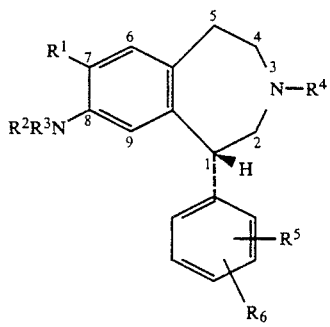

wherein
R$^1$ is hydrogen, halogen, alkyl, alkoxy, or trifluoromethyl;
R$^2$ is hydrogen, alkyl, arylalkyl or COXR$^a$ (wherein R$^a$ is hydrogen or alkyl and X is a bond or NH);
R$^3$ is hydrogen or alkyl;
R$^4$ is alkyl, —CH$_2$CH=CH$_2$ or

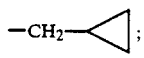

R$^5$ and R$^6$ are the same or different and are independently selected from hydrogen, alkyl, trifluoromethyl, halogen, OR$^a$ (wherein R$^a$ is defined above) or together R$^5$ and R$^6$ form —OCH$_2$O—; and the pharmaceutically acceptable salts thereof.

2. The compounds defined in claim 1 wherein
R$^1$ is halogen, methyl or trifluoromethyl;
R$^2$ is hydrogen, methyl, formyl or acetyl;
R$^3$ is hydrogen;
R$^4$ is methyl or —CH$_2$CH=CH$_2$;
R$^5$ is hydrogen, methyl, halogen or OR$^a$;
R$^6$ is hydrogen;
and the pharmaceutically acceptable salts thereof.

3. The compounds defined in claim 2 wherein R$^5$ is hydrogen; and the pharmaceutically acceptable salts thereof.

4. The compounds defined in claim 1 wherein R$^4$ is methyl, and the pharmaceutically acceptable salts thereof.

5. The compounds defined in claim 1 wherein R$^1$ is halogen, and the pharmaceutically acceptable salts thereof.

6. The compounds defined in claim 1 wherein R$^1$ is chlorine, and the pharmaceutically acceptable salts thereof.

7. The compounds defined in claim 1 wherein R$^1$ is methyl, and the pharmaceutically acceptable salts thereof.

8. The compounds defined in claim 1 wherein R$^2$ and R$^3$ are both hydrogen, and the pharmaceutically acceptable salts thereof.

9. The compounds defined in claim 1 wherein R$^5$ and R$^6$ are both hydrogen, and the pharmaceutically acceptable salts thereof.

10. The compounds defined in claim 2 wherein R$^3$ is hydrogen, and the pharmaceutically acceptable salts thereof.

11. The compounds defined in claim 3 wherein R$^3$ is hydrogen, and the pharmaceutically acceptable salts thereof.

12. The compounds defined in claim 10 wherein R$^1$ is halogen, and the pharmaceutically acceptable sales thereof.

13. The compounds defined in claim 12 wherein R$^1$ is chlorine, and the pharmaceutically acceptable salts thereof.

14. The compounds defined in claim 4 wherein R$^2$ and R$^3$ are both hydrogen, and the pharmaceutically acceptable salt thereof.

15. The compounds defined in claim 5 wherein R$^2$ and R$^3$ are both hydrogen, and the pharmaceutically acceptable salt thereof.

16. The compounds defined in claim 15 wherein R$^1$ is chlorine, and the pharmaceutically acceptable salts thereof.

17. The compounds defined in claim 16 wherein R$^5$ and R$^6$ are both hydrogen and the pharmaceutically acceptable salts thereof.

18. The compound defined in claim 1 which has the name, (R)-8-amino-7-chloro-3-methyl-1-phenyl-2,3,4,5-tetrahydro-1H-3-benzazepine, and the pharmaceutically acceptable salts thereof.

19. The compound defined in claim 18 which is the maleate salt.

20. The compound defined in claim 1 which has the name, (R)-8-formamido-7-chloro-3-methyl-1-phenyl-2,3,4,5-tetrahydro-1H-3-benzazepine, and the pharmaceutically acceptable salts thereof.

21. The compound defined in claim 1 which has the name, (R)-8-methylamino-7-chloro-3-methyl-1-phenyl-2,3,4,5-tetrahydro-1H-3-benzazepine, and the pharmaceutically acceptable salts thereof.

22. The compound defined in claim 1 which has the name, (R)-8-acetamido-7-chloro-3-methyl-1-phenyl-2,3,4,5-tetrahydro-1H-3-benzazepine, and the pharmaceutically acceptable salts thereof.

23. The compound defined in claim 1 which has the name, (R)-8-dimethylamino-7-chloro-3-methyl-1-phenyl-2,3,4,5-tetrahydro-1H-3-benzazepine, and the pharmaceutically acceptable salts thereof.

24. The compound defined in claim 1 which has the name, (R)-8-ethylamino-7-chloro-3-methyl-1-phenyl-2,3,4,5-tetrahydro-1H-3-benzazepine, and the pharmaceutically acceptable salts thereof.

25. A compound having the structural formula:

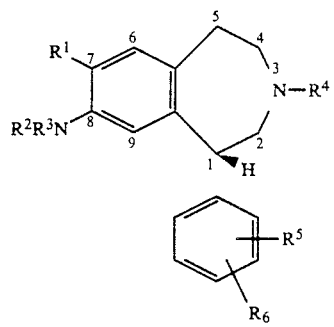

wherein the absolute stereochemical configuration at carbon 1 is as depicted,
R$^1$ is hydrogen, halogen, alkyl, alkoxy, or trifluoromethyl;
R$^2$ is hydrogen, alkyl, arylalkyl or COXR$^a$ (wherein $R^a$ is hydrogen or alkyl and X is a bond or NH);
$R^3$ is hydrogen or alkyl; or
$R^2$ and $R^3$ taken together with the nitrogen atom to which they are attached form

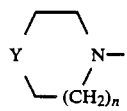

wherein Y is O, $CH_2$ or $NR^a$ (wherein $R^a$ is as defined above) and n is 0, 1 or 2 provided that n is not 0 when Y is O or $NR^a$;

$R^4$ is alkyl, $-CH_2CH=CH_2$ or

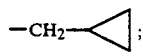

$R^5$ and $R^6$ are the same or different and are independently selected from hydrogen, alkyl, trifluoromethyl, halogen, $OR^a$ (wherein $R^a$ is defined above) or together $R^5$ and $R^6$ form $-OCH_2O-$; and the pharmaceutically acceptable salts thereof.

26. The compound defined in claim 25 which has the name, (R)-8-amino-3,7-dimethyl-1-phenyl-2,3,4,5-tetrahydro-1H-3-benzazepine, and the pharmaceutically acceptable salts thereof.

27. The compound defined in claim 26 which is the maleate salt.

28. A composition useful for treating psychoses in a mammal which comprises a compound having the structural formula defined in claim 23 or a pharmaceutically acceptable salt thereof in combination with a pharmaceutically acceptable carrier.

29. A method for treating psychoses in a mammal which comprises administering an effective amount of the pharmaceutical composition defined in claim 20 to said mammal.

30. A composition useful for treating depression in a mammal which comprises a compound having the structural formula defined in claim 23 or a pharmaceutically acceptable salt thereof in combination with a pharmaceutically acceptable carrier.

31. A method for treating depression in a mammal which comprises administering an antidepressant effective amount of the pharmaceutical composition defined in claim 30 to said mammal.

32. A composition useful for treating psychoses in a mammal which comprises a compound of structural formula I as defined in claim 1 in combination with a pharmaceutically acceptable carrier.

33. A method for treating psychoses in a mammal which comprises administering an effective amount of the composition defined in claim 32 to said mammal.

34. A composition useful for treating depression in a mammal which comprises a compound of structural formula I as defined in claim 1 in combination with a pharmaceutically acceptable carrier.

35. A method for treating depression in a mammal which comprises administering an antidepressant effective amount of the composition defined in claim 34 to said mammal.

* * * * *